United States Patent [19]

Shepherd

[11] 4,348,399
[45] Sep. 7, 1982

[54] ANTIATHEROSCLEROTIC AND HYPOLIPIDEMIC 4-(MONOALKYLAMINO)PHENYL ALKANE, ALKENE AND ALKYNE CARBINOLS, ALDEHYDES, CARBOXYLIC ACIDS AND DERIVATIVES

[75] Inventor: Robert G. Shepherd, South Nyack, N.Y.

[73] Assignee: American Cyanamid Company, Stamford, Conn.

[21] Appl. No.: 874,431

[22] Filed: Feb. 2, 1978

[51] Int. Cl.³ .................... A61K 31/44; C07C 59/56; C07C 101/48; A61K 31/19; A61K 31/20; A61K 31/235; A61K 31/24; A61K 31/27
[52] U.S. Cl. ...................................... 424/263; 560/19; 562/472; 562/473; 562/458; 260/326.41; 564/163; 542/420; 546/300; 546/335; 424/317; 424/318; 424/308; 424/309; 424/300

[58] Field of Search .................... 260/518 A, 326.41; 560/19; 562/472, 473, 458; 564/163; 542/420; 546/300, 335; 424/263, 317, 318, 308, 309, 300

[56] References Cited

U.S. PATENT DOCUMENTS 3,692,819  9/1972  Carney et al. .................... 560/19 X
3,868,416  2/1975  Albright et al. .................. 560/19 X
3,957,850  5/1976  Bouchara ......................... 560/19 X

OTHER PUBLICATIONS

Parker, Journal of Medicinal Chemistry, 1977, vol. 20, No. 6, pp. 781-791.

Primary Examiner—Henry R. Jiles
Assistant Examiner—Robert C. Whittenbaugh
Attorney, Agent, or Firm—Jack W. Richards

[57] ABSTRACT

This disclosure describes novel 4-(monoalkylamino)-phenyl alkane, alkene and alkyne carbinols, aldehydes, carboxylic acids and derivatives useful as hypolipidemic and antiatherosclerotic agents.

7 Claims, No Drawings

ANTIATHEROSCLEROTIC AND HYPOLIPIDEMIC 4-(MONOALKYLAMINO)PHENYL ALKANE, ALKENE AND ALKYNE CARBINOLS, ALDEHYDES, CARBOXYLIC ACIDS AND DERIVATIVES

BRIEF SUMMARY OF THE INVENTION

This invention describes new organic compounds, more particularly, 4-(monoalkylamino)phenyl alkane, alkene and alkyne carbinols, aldehydes, carboxylic acids and derivatives thereof, of the following structural formula:

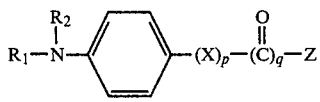

wherein $R_1$ is an unbranched or branched alkyl group $C_nH_{2n+1}$ wherein n is an integer from 8 to 19; $R_2$ is hydrogen or a group convertible in vivo thereinto such as, most notably, methyl, ethyl, carboxymethyl, acetyl, trifluoroacetyl, succinyl, 1-(sodium sulfo)lower alkyl, 1-(sodium sulfo)polyhydroxy alkyl, and 1,3-bis(sodium sulfo)aralkyl; X is selected from a group consisting of branched or unbranched $C_1$–$C_4$alkylene, $C_2$–$C_4$-alkenylene, and $C_2$–$C_4$alkynylene; subscripts p and q may be 0 or 1 providing that the sum of p and q must be 1 or 2; Z is selected from the group consisting of carboxyl, formyl, imidoyl, substituted and unsubstituted carbamoyl, hydroxyl (with the proviso that q is then 0 and X consists of two or more carbon atoms) and COOR$_3$ wherein $R_3$ is selected from the group consisting of $C_1$–$C_4$ branched and unbranched alkyl, ($C_1$–$C_3$ alkoxy)loweralkyl, di($C_1$–$C_3$alkyl)aminolower alkyl, $C_1$–$C_3$ mono- or dihydroxyalkyl, mononuclear aryl, arylmethyl, $C_3$–$C_5$ carboalkoxyalkyl, and $C_2$–$C_5$ carboxyalkyl and the pharmaceutically acceptable acid-addition and cationic salts thereof.

Suitable alkyl groups represented by $R_1$ are heptadecyl, hexadecyl, pentadecyl, tetradecyl, nonyl and the like.

Suitable branched alkyl groups for the substituent $R_1$ may be, for example, 1-methylpentadecyl, 1-ethyltetradecyl, 1-heptylnonyl, 2-ethyldodecyl, 1,4-diethyloctyl, 11-methyldodecyl, 5,5-dimethylhexyl, 4,8,12-trimethyltridecyl, 2,4,6,8-tetramethylnonyl, 1,4-dimethyl-1-ethylhexyl, 15-methylhexadecyl, 14-methylpentadecyl, 13,13-dimethyltetradecyl, 15,15-dimethylhexadecyl, and the like.

Suitable ester moieties COOR$_3$ contemplated by the present invention are those where $R_3$ are groups such as ethyl, benzyl, pyridylmethyl, 2-ethoxyethyl, 2-dimethylaminoethyl, glyceryl, 3-methoxy-2-hydroxypropyl, 2,3-epoxypropyl, 2- and 3-hydroxypropyl, phenyl, 3-pyridyl, carboethoxymethyl, and carboxymethyl.

Suitable moieties contemplated by the present invention and represented by X are methylene, ethylene, propylene, vinylene, ethynylene, butadienylene, and the like.

A preferred embodiment of this invention is represented by the following structural formula:

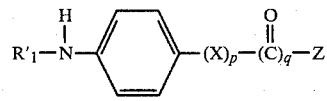

wherein $R_1'$ is a branched or unbranched alkyl group $C_nH_{2n+1}$ wherein n is an integer 13 to 17 inclusive; X, p, q and Z are defined as above.

A more preferred embodiment is represented by the structural formula:

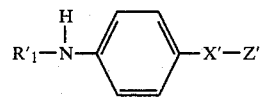

wherein X' is selected from the group consisting of a branched or unbranched $C_1$–$C_3$ alkyl, $C_2$–$C_4$ alkenyl, or ethynyl; Z' is selected from the group consisting of carboxyl, substituted carbamoyl, formyl and COOR$_3$ wherein $R_3$ and $R_1'$ are defined as herein above.

A most preferred embodiment of this invention is represented by the following structural formula:

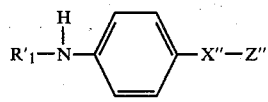

wherein X'' is $C_1$–$C_3$ alkyl or vinyl; Z'' is carboxyl, formyl or COOR$_3$ wherein $R_3$ and $R_1'$ are defined as herein above.

The invention also pertains to novel compositions of matter useful as antiatherosclerotic agents and to methods of meliorating atherosclerosis by counteracting hyperlipemia and arterial plaque formation in mammals therewith; the active ingredients of said compositions of matter being the novel 4-(monoalkylamino)phenyl compounds of the present invention. These compounds may be utilized either as the free bases or in the form of a pharmaceutically acceptable salt with an organic or inorganic acid or base. The invention also contemplates a method for lowering serum lipids and for ameliorating atherosclerosis in mammals by the administration of said compounds.

BACKGROUND OF THE INVENTION

Considerable effort has been directed in recent years to obtain substances useful in counteracting the consequences of hyperlipidemia, a condition involving elevated cholesterol, phospholipid and/or triglyceride levels in the blood, and of hyperlipoproteinemia, involving an imbalance of the lipoproteins. The most serious condition associated with hyperlipidemia and hyperlipoproteinemia is atherosclerosis, a form of arteriosclerosis characterized by lipid accumulation and thickening of the walls of both medium-sized and large arteries such as the aorta. Their walls are thereby weakened and the elasticity and effective internal size of the arteries decreased. Atherosclerosis, the most common cause of coronary artery disease, is of great medical importance since it tends to occlude those arteries supplying blood to the heart muscles and brain, thereby producing permanent damage to these organs. Such damage may lead to ischemic heart disease, congestive heart failure, life-threatening arrhythmias, senility, or stroke. Involvement of leg arteries may lead to gangrene and loss of the limb. It has been known for more than 100 years that cholesterol is a major component of atherosclerotic lesions or plaques. Investigators have been trying to determine the role of cholesterol in lesion initiation and development and also, most importantly, whether lesion formation can be prevented or reversed and enlargement of lesions be slowed or stopped. The earliest lesions are now known to be fatty streaks, largely of cholesterol, which often progress in stages to plaques containing cellular, fibrous and calcified material in addition to the lipids.

The evidence that hyperlipidemia is one of the factors involved in coronary heart disease is very impressive. A most important study carried out in Framingham, Mass. (Gordon & Verter, 1969) in over 5,000 persons for more than 12 years established a correlation between high concentrations of blood cholesterol and increased risk of heart attack. Although the causes of coronary artery disease are multiple, one of the most constant factors has been the elevated concentration of lipids in the blood plasma. A combined elevation of cholesterol and triglycerides has been shown (Carlson & Bottiger, 1972) to carry the highest risk of coronary heart disease. The majority of patients with ischemic heart disease or peripheral vascular disease were found to have hyperlipoproteinemia, involving very low-density and/or low-density lipoproteins (Lewis et al. 1974).

The reason for most treatment of hyperlipidemia or hyperlipoproteinemia is for arresting, reversing or preventing atherosclerosis. In the past, attempts have been made to lower the levels of cholesterol, phospholipids, and triglycerides in the blood by the oral feeding of various substances which have been generally referred to in the art as hypolipidemic agents or hypocholesteremic adjuvants. Typical of such substances are lecithin, pectin, cottonseed oil, and the mucilaginous substances listed in U.S. Pat. No. 3,148,114. In addition, several synthetic hypolipidemic agents are now available, namely, clofibrate, D-thyroxine, cholestyramine and nicotinic acid [(Levy & Frederickson, Postgraduate Medicine 47, 130 (1970)]. Clofibrate has the undesirable side-effect of causing hypertrophy of the liver in some patients.

The development of agents capable of reducing elevated blood lipids and of favorably altering blood-lipoprotein patterns is considered by medical authorities to be extremely important for the treatment and prevention of atherosclerosis.

DETAILED DESCRIPTION OF THE INVENTION

The compounds of this invention are new and novel 4-(monoalkylamino)phenyl alkane, alkene and alkyne carbinols, aldehydes, carboxylic acids and derivatives and have useful biological and pharmacological properties. No hypolipidemic activity has been reported in the literature for these compounds and they are different in structure from other hypolipidemic agents. The compounds of this invention lower serumlipid concentrations and also minimize atheroma formation in the aorta. These substances provide the oral administration required of hypolipidemic agents, which patients usually take for many years. The 4-(alkylamino)benzoic acids and esters were disclosed in U.S. Pat. No. 3,868,416.

We have now found that the compounds of the present invention can safely and effectively lower both serum sterols and triglycerides in warm-blooded mammals. Such actions on serum lipid components are considered to be very useful in the treatment of atherosclerosis, especially in contrast to available drugs whose action is much more limited. For some time it has been considered desirable to lower serum lipid levels and to correct lipoprotein imbalance in mammals as a preventive measure against atherosclerosis. The compounds of the present invention do not act by blocking late stages of cholesterol biosynthesis and thus do not produce accumulation of intermediates such as desmosterol, as equally undesirable as cholesterol itself. Compounds with the combination of therapeutically favorable characteristics possessed by those of the present invention can be safely administered to warm-blooded mammals for the treatment of hyperlipidemic and atherosclerotic states found in patients with or prone to heart attacks, to peripheral or cerebral vascular disease, and to stroke.

The novel compounds of the present invention are, in general, white crystalline solids having characeristic melting points and absorption spectra. They are soluble in organic solvents such as lower alkanols, chloroform, benzene, dimethylformamide, and the like but are generally not very soluble in water. The novel compounds of the present invention, which are organic bases, may be converted to their non-toxic acid-addition salts with a variety of pharmaceutically acceptable organic and inorganic salt-forming reagents. Thus, acid-addition salts may be formed by admixture of the organic free base in a neutral solvent with one or two equivalents of an acid such as sulfuric, phosphoric, hydrochloric, hydrobromic, trifluoroacetic, citric, tartaric, ascorbic, and the like. The compounds which contain acidic groups form pharmaceutically acceptable cationic salts with organic or inorganic bases such as the alkali metal hydroxides, the alkaline earth metal hydroxides, and the like.

The N-alkylanilines of the present invention are prepared by reaction of the appropriate aminophenyl compounds with suitable alkylating agents such as alkyl halides, sulfates, tosylates or trifluoromethanesulfonates with or without solvent at 30°–150° C. Suitable solvents are lower alkanols, N,N-dimethylformamide, N,N-dimethylacetamide, diglyme, acetonitrile, toluene, benzene, hexamethylphosphoramide and the like. The reaction may be carried out with 2 equivalents of the aminophenyl substrate or with one equivalent plus an equivalent of base such as an unreactive organic base such as diisopropylethylamine or an alkali carbonate or bicarbonate or with a catalytic amount of copper powder when alkyl halides are used as the alkylating agent. Similar alkylation of the sodium salt (formed with sodium hydride) of the anilide moiety of 4-acetaminophenyl compounds yields the N-acetyl compounds of structure I, which are also prepared by acylation of (4-alkylamino)phenyl compounds.

Alternative methods of preparation are by reductive alkylation of a 4-aminophenyl compound which may also be generated in situ by reduction of 4-amino precursors such as a 4-nitro group and the like or by a hydride (diborane) reduction of a 4-(acylamino)phenyl compound in a special procedure. In reductive alkylation for example, n-hexadecanal or other carbonylalkanes and 4-aminophenylpropionic acid are reduced under 1–10 atmospheres of hydrogen using an activated metal catalyst forming 4-(hexadecylamino)phenylpropionic acid and the like. Diborane reduction of 4-(hexadecanoylamino)phenyl compounds formed by acylation of 4-aminophenyl compounds ethyl 4-(hexadecanoylamino)phenylpropionate at room temperature or above for 1-6 hours yields some product from reduction of the ester moiety as well as the desired corresponding 4-(hexadecylamino)phenyl analogs. Therefore, in order to prepare the 4-(alkylamino)phenyl alkanoic, alkenoic and alkynoic acid esters it is advantageous to form the corresponding alkylchloroimide from hexadecanoylaminophenyl esters such as ethyl 4-(hexadecanoylamino)phenylpropionate with phosphorus oxychloride and base, and then reduce the chloroimide moiety to alkylamino with sodium borohydride.

The 4-(monoalkylamino)phenyl carboxylic acids of this invention are often prepared from their corresponding p-aminophenyl carboxylic acid by the sequence involving esterification of the carboxylic acid with ethanol, followed by alkylation of the amino function with the $C_8$ to $C_{19}$ alkyl bromide and potassium carbonate in hexamethylphosphoramide at 40°-140° C. for 2-20 hours. The free acids are then liberated by hydrolysis of the ester with aqueous alcoholic sodium hydroxide at 80° for 2-10 hours; the resulting sodium salts are then treated with dilute mineral acid to form the carboxylic acid. Alternatively, the free acids may be prepared by hydrolysis of the corresponding nitriles or various amides. The carboxylic moiety is also generated by oxidation of the corresponding aldehydes, most often with use of an amine-protecting group such as trifluoroacetyl or t-butoxycarbonyl. The 4-aminophenyl carboxylic acids used as starting materials are commercially available or prepared by methods described herein.

The 4-aminophenylalkenoic acids, if not commercially available, are prepared by condensation of the appropriate aldehydes or by dehydration of 4-(alkylamino)phenylcarbinolalkanoic acids. For example, 5-(p-hexadecylaminophenyl)-2,4-pentadienoic acid ethyl ester is obtained by the Wittig reaction of 4-(hexadecylamino)benzaldehyde with the Wittig reagent, triethyl 4-phosphonocrotonate. These alkenoic acids are also prepared by heating 4-(N-decyl-N-methylamino)benzaldehyde and the like with sodium ethyl acetate carbanion or with a mixture of ethyl acetate, acetic anhydride and potassium acetate. The second method is illustrated by dehydration of ethyl 3-(4-alkylaminophenyl)-3-hydroxypropionate to yield ethyl-3-(4-alkylamino)cinnamate. The acetylenic analogs result from dehydrobromination of ethyl 3-(alkylaminophenyl)-2,3-dibromopropionate, its isomers, or N-acyl analogs to form ethyl 4-(alkylamino)phenylpropiolate and the like. The acetylenic acids are also formed from 4-(alkylamino)phenylacetylene metal salts by carboxylation with carbon dioxide. The 4-(alkylamino)phenylacetylenes are also used by (a) N-acylation with t-butyl azidoformate and (b) conversion to the lithium acetylide salt and reaction in tetrahydrofuran at −20° with borontrifluoride etherate to form the corresponding triaralkynylborane, $(RR'NC_6H_4C\equiv C)_3B$. The latter in the same solution at −20° is reacted with ethyl diazoacetate followed by water to yield the butynoic ester $4\text{-}RR'NC_6H_4C\equiv CCH_2COOC_2H_5$.

The 4-hexadecylaminophenylalkyl carbinols of this invention are easily obtained by reduction of the corresponding ethyl esters with lithium aluminum hydride in ether at 20° C.

The novel esters and amides of the present invention may be readily prepared by treating an acid halide, mixed acid anhydride, or activated ester or amide of the formulae:

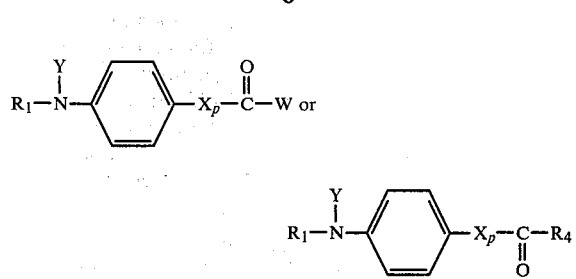

wherein W is chloro or bromo, $R_4$ is an activated ester or amide moiety or an acyl group and $R_1$ is as hereinabove defined; with a hydroxy compound or an amine or a salt of a carboxamide or sulfonamide. These reactions are preferably carried out in an inert solvent at a temperature of 50°-125° C. for a period of time of from about 30 minutes to 18 hours or more. In the case of the acid halide and other acid-forming acylating agents, the reaction is carried out in the presence of an acid scavenger such as diisopropylethylamine, 4-dimethylaminopyridine, pyridine, triethylamine, finely powdered sodium carbonate, and the like. A protecting group Y on the arylamine nitrogen is used for best results. The simplest protecting group is provided by double protonation of the amine to give an anilinium salt prior to or during formation of the acylating form of the carboxyl group. Acylation of this anilino group by carefully selected acyl groups such as carbobenzyloxy, carbo-t-butoxy, and trifluoroacetyl provides protection of this group from self-acylation during amide formation. These protecting groups are then removed by catalytic hydrogenation, mild acid treatment, and mild alkali treatment, respectively. Other N-acyl groups such as acetyl, succinoyl and the like are removed by conventional methods. Activated esters and amides, useful to synthesize the esters and amides of the present invention, are carboxymethyl, 4-nitropheyl, N-oxysuccinimide, 1-imidazolyl and the like. In certain cases, treatment of the acids with an excess of an appropriate hydroxy-containing substrate in the presence of a Lewis or mineral acid such as boron trifluoride, sulfuric acid, or hydrochloric acid is sufficient to convert the 4-(monoalkylamino)phenyl acids to the corresponding esters. To form certain esters, it is convenient to form the alkali metal or strong organic base salts of the 4-(monoalkylamino)phenyl acids in order to react them with various halo compounds.

The imidates of the present invention are prepared by (1) acid-catalyzed addition of hydroxyalkanes to the corresponding nitriles or (2) intramolecular formation from 2-haloethyl or 3-halopropyl amides as well as from 2-hydroxyethyl or 3-hydroxypropyl amides when treated with a condensing agent such as thionyl chloride.

The 4-(alkylamino)phenylalkanoic acids, amides or esters are also prepared by catalytic reduction, at 1 to 10 atmospheres of hydrogen, of the corresponding alkenoic or alkynoic derivatives.

Reduction of nitriles such as 4-(hexadecylamino)hydrocinnamonitrile with stannic chloride and anhydrous hydrogen chloride gas, followed by hydrolysis in hot water provides 4-hexadecylaminohydrocinnamaldehyde (and analogous aldehydes) of interest. This reduction is also conveniently done by metal hydrides such as diisobutyl aluminum hydride.

The 4-(alkylamino)phenylalkanoic acids and derivatives are prepared by Friedel-Crafts acylation of the N-acyl-N-alkylanilines with the appropriate dicarboxylic acid anhydride or half acid chloride. The 4-(alkylamino)benzoylalkanoic acids or esters obtained by this and by other syntheses are converted to the 4-(alkylamino)phenylalkanoic acids, when desired, by reduction with (a) hydrazine and alkali in diethyleneglycol at 140° for 3 hours, (b) zinc amalgam and ethanolic hydrochloric acid at 60° for 5 hours, (c) red phosphorus and hydriodic acid, or (d) ketalization with 1,2-ethanedithiol followed by Raney nickel desulfurization. The amides of the 4-(alkylamino)phenylalkanoic acids are prepared by heating the corresponding 4-(alkylamino)phenyl alkyl ketones with aqueous alcoholic ammonium polysulfide; hydrolysis yields the acids with the same number of carbon atoms as the ketone. These acids are also prepared by reacting 4-(N-t-butyloxycarbonyl-N-alkylamino)phenylmagnesium halides with 2-(3-halopropyl)-2-oxazolines, followed by mild acid liberation of the carboxyl group from its protected form as the 2-oxazoline, thus forming the 4-(alkylamino)-phenylalkanoic acid after removal of the amine-protecting group. Similarly, the above Grignard reagent can be reacted with 3-bromo triethyl orthopropionate in the presence of dilithiumtetrachlorocuprate to yield the desired acids after removal of the protecting groups from the amino and carboxyl groups.

The novel compounds of the present invention are not only potent hypolipidemic agents but also prevent or diminish the formation or enlargement of arterial plaques in mammals when administered in amounts ranging from about one milligram to about 250 mg. per kilogram of body weight per day. A preferred dosage regimen for optimum results would be from about 5 mg. to about 100 mg. per kilogram of body weight per day, and such dosage units are employed that a total of from about 0.15 gram to about 7.0 grams of the active compound for a subject of about 70 kg. of body weight are administered in a 24 hour period. This dosage regimen may be adjusted to provide the optimum therapeutic response. For example, several divided doses may be administered daily or the dose may be proportionally reduced as indicated by the exigencies of the therapeutic situation. A decided practical advantage of this invention is that the active compound may be administered in a convenient manner by the oral route. The compounds of the present invention exert a more powerful hypocholesteremic and antiatherosclerotic effect than the aforementioned adjuvants and synthetic medicaments. It is not known how these novel compounds operate in the blood serum and no theory of why these compounds so operate is advanced. It is not intended that the present invention should be limited to any particular mechanism of action of lowering serum lipids or of ameliorating atherosclerosis, or be limited to compounds acting by only one mechanism.

The active compounds of the present invention may be orally administered, for example, with an inert diluent or with an assimilable edible carrier, or they may be enclosed in hard or soft shell gelatin capsules, or they may be compressed into tablets, or they may be incorporated directly with food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active ingredient in such therapeutically useful compositions is such that a suitable dosage will be obtained. Preferred compositions or preparations according to the present invention are prepared so that an oral dosage-unit form contains between about 50 and 250 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage-unit form is a capsule, it may contain, in addition to materials of the above type, a liquid carrier. Various other materials may be present as coatings or otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye, and flavoring such as cherry or orange flavor. Of course, any material used in preparing any dosage-unit form should be pharmaceutically pure and substantially non-toxic in the amounts employed. In addition, the active ingredients may be incorporated into sustained-release preparations and formulations.

The invention will be described in greater detail in conjunction with the following specific examples.

EXAMPLE 1

Ethyl (4-hexadecylamino-phenyl)acetate

A solution of 8.2 g. of p-aminophenylacetic acid, 150 ml. of absolute ethanol, and 3 ml. of boron trifluoride etherate is heated to reflux for 15 hrs. The solution is concentrated to ca. 50 ml. by distillation of the solvent and then evaporated to dryness in vacuo. The residue is dissolved in ethyl ether, washed with aqueous sodium bicarbonate, dried and evaporated to yield ethyl p-aminophenylacetate. A mixture of 5.0 g. of this amine, 9.4 g. of 1-bromohexadecane, 4.2 g. of anhydrous potassium carbonate and 40 ml. of hexamethylphosphoramide is heated to 80° C. for 7 hours. The mixture is then cooled, diluted with water and extracted with ethyl ether. The ether extracts are washed with water, dried and evaporated. The residue is recrystallized from a mixture of chloroform and hexane, yielding ethyl (4-hexadecylaminophenyl)acetate.

Similarly prepared from p-aminophenylacetic acid are ethyl (4-nonadecylaminophenyl)acetate, ethyl (4-pentadecylaminophenyl)acetate, ethyl (4-decylaminophenyl)acetate, ethyl (4-octylaminophenyl)acetate, ethyl [4-[(1-methylpentadecyl)amino]phenyl]acetate, ethyl [4-[(2,4,6,8-tetramethylnonyl)amino]phenyl]acetate and ethyl [4-[(15-methylhexadecyl)amino]phenyl]acetate.

EXAMPLE 2

(4-Hexadecylaminophenyl)acetic acid

A mixture of 6.0 g. of ethyl (4-hexadecylaminophenyl)acetate, 7.0 g. of potassium hydroxide and 100 ml. of ethanol-water (9:1) is heated to reflux for 4 hours. While hot, the mixture is adjusted to pH 7 with conc. hydrochloric acid. The mixture is diluted with water cooled and filtered. Recrystallization of the precipitate yields (4-hexadecylaminophenyl)acetic acid.

Similarly prepared from their corresponding ethyl esters are (4-nonadecylaminophenyl)acetic acid, (4-pentadecylaminophenyl)acetic acid, (4-decylaminophenyl)acetic acid, (4-octylaminophenyl)acetic acid, [4-[(1-methylpentadecyl)amino]phenyl]acetic acid, [4-[(2,4,6,8-tetramethylnonyl)amino]phenyl]acetic acid, and [4-[(15-methylhexadecyl)amino]phenyl]acetic acid.

EXAMPLE 3

Ethyl 4-(hexadecylamino)hydrocinnamate

A mixture of 5.0 g. of p-nitrocinnamic acid and 100 mg. of 10% palladium on carbon in 200 ml. of ethanol containing 5 drops of 5.5 N ethanolic HCl is treated with hydrogen in a Parr apparatus at room temperature for 3 hours. The mixture is then filtered through celite and the filtrate is concentrated, affording p-amino hydrocinnamic acid.

A solution of 10.0 g. p-aminohydrocinnamic acid in 100 ml. of absolute ethanol containing 16 ml. of boron trifluoride etherate is heated to reflux for 48 hours. The solution is then cooled, poured into 5% aqueous sodium carbonate, and extracted with methylene chloride. Evaporation of the organic extracts yields ethyl p-aminohydrocinnamate.

In a manner according to Example 1, ethyl p-aminohydrocinnamate is alkylated with 1-bromohexadecane and potassium carbonate in hexamethylphosphoramide, providing ethyl 4-(hexadecylamino)hydrocinnamate.

In a similar manner, the following esters are prepared: ethyl 4-(nonadecylamino)hydrocinnamate, ethyl 4-(tetradecylamino)hydrocinnamate, ethyl 4-(octylamino)hydrocinnamate, ethyl 4-[(1-methylpentadecyl)amino]hydrocinnamate, ethyl 4-[(14-methylpentadecyl)amino]hydrocinnamate and ethyl 4-(decylamino)hydrocinnamate.

EXAMPLE 4

4-(Hexadecylamino)hydrocinnamic acid

In a manner analogous to that described in Example 2, ethyl 4-hexadecylaminohydrocinnamate is hydrolyzed with potassium hydroxide to 4-(hexadecylamino)hydrocinnamic acid.

Similarly prepared by hydrolysis of the corresponding ester are 4-(nonadecylamino)hydrocinnamic acid, 4-(tetradecylamino)hydrocinnamic acid, 4-(octylamino)hydrocinnamic acid, 4-[(1-methylpentadecyl)amino]hydrocinnamic acid, 4-[(14-methylpentadecyl)amino]hydrocinnamic acid, and 4-(decylamino)hydrocinnamic acid.

EXAMPLE 5

Ethyl 4-(N-hexadecylacetamido)hydrocinnamate

A mixture of 10.0 g. of ethyl 4-(hexadecylamino)hydrocinnamate, 50 ml. of pyridine and 25 ml. of acetic anhydride is heated on a steam bath for 15 hours. The solution is poured onto ice and adjusted to pH 6 with concentrated hydrochloric acid. The mixture is filtered and the crystals washed with water. The solid is recrystallized from ethanol, yielding ethyl 4-(N-hexadecylacetamido)hydrocinnamate.

EXAMPLE 6 p-(Hexadecylmethylamino)hydrocinnamic acid

A solution of 7.8 g. of ethyl 4-hexadecylaminohydrocinnamate in 125 ml. of methylene chloride and 5 ml. of methyl fluorosulfonate is stirred at room temperature for 20 hours. The mixture is poured onto ice and made basic with 10 N sodium hydroxide. The layers are separated and the aqueous phase is extracted with methylene chloride. The combined organic extracts are dried and evaporated, yielding ethyl p-hexadecylmethylaminohydrocinnamate. Hydrolysis of this ester as in Example 2 provides the title compound.

EXAMPLE 7

4-(Hexadecylamino)cinnamic acid and ethyl ester

A mixture of ethyl p-aminocinnamate, one equivalent of 1-bromohexadecene, one equivalent of anhydrous potassium carbonate in hexamethylphosphoramide is heated for 20 hours at 60° C. The mixture is then cooled, diluted with water and extracted with ether. The combined ether extracts are dried, filtered and evaporated to provide ethyl 4-hexadecylaminocinnamate. The ester is hydrolyzed with sodium hydroxide in a 1:1 water:ethanol solution at steam bath temperature for 10 hours. The hot solution is then acidified with acetic acid, cooled, filtered and the precipitate is washed with water. Recrystallization from chloroform yields 4-hexadecylaminocinnamic acid.

Similarly prepared are: 4-(nonadecylamino)cinnamic acid, 4-(tetradecylamino)cinnamic acid, 4-(decylamino)cinnamic acid, 4-(octylamino)cinnamic acid and 4-(1-methylpentadecylamino)cinnamic acid.

EXAMPLE 8

4-(4-Hexadecylaminophenyl)butyric acid

A solution of 10.0 g. of 4-(4-nitrophenyl)butyric acid in 150 ml. of ethanol containing 50 mg. of a 10% palladium on carbon catalyst is hydrogenated until the uptake of hydrogen ceases. After the system is purged with nitrogen and the solution is filtered through a celite pad, 3 ml. of boron trifluoride etherate is added and the solution is heated to reflux for 10 hours. Upon cooling and evaporation of the ethanol, a colorless residue is obtained. This product is recrystallized from ethanol-hexane and affords ethyl 4-(4-aminophenyl)butyrate.

A sample of ethyl 4-(4-aminophenyl)-butyrate is alkylated and subsequently hydrolyzed as described in Example 7 to yield 4-(4-hexadecylaminophenyl)butyric acid.

Similarly prepared are 4-(4-nonadecylaminophenyl)butyric acid, 4-(4-tridecylaminophenyl)butyric acid, [4-[4-(1-methylpentadecyl)amino]phenyl]butyric acid, and 4-[4-(11-methyldodecylamino)phenyl]butyric acid.

EXAMPLE 9

(4-Hexadecylaminophenyl)propiolic acid

A sample of 50 g. of ethyl p-aminocinnamate is dissolved in 500 ml. of ethyl ether and a solution of 50 g. of trifluoroacetic anhydride in 30 ml. of ether is added dropwise. When the addition is complete, the reaction is allowed to stir for another hour. The mixture is then diluted with hexane and filtered, providing ethyl p-(trifluoroacetamido)cinnamate.

A solution of 40 g. of ethyl p-(trifluoroacetamido)cinnamate in 200 ml. of carbon tetrachloride is cooled in ice. Bromine (28 g.) is added dropwise, the reaction is allowed to stir for one additional hour, and then the solvent is evaporated. The crystalline residue is the dibromo ester.

A solution of 11.4 g. (0.204 mole) of potassium hydroxide in 300 ml. of 95 percent ethanol is cooled to 40° C. and 20 g. (0.051 mole) of the crude dibromo ester above is added. After 30 minutes, the reaction is heated to reflux for five hours. The solution is then cooled and filtered. The filtrate is treated with acetic acid until the solvent is neutral to litmus, then concentrated, chilled and filtered, providing p-aminophenylpropiolic acid.

The esterification of p-aminophenylpropiolic acid with ethanol and boron trifluoride etherate as in Example 1 provides ethyl p-aminophenylpropiolate.

As in Example 7, ethyl p-aminophenylpropiolate is alkylated with 1-bromohexadecane, and subsequently hydrolyzed with potassium hydroxide to afford (4-hexadecylaminophenyl)propiolic acid.

Analogous alkylations of ethyl p-aminophenylpropiolate, followed by basic hydrolysis, provides (4-tetradecylaminophenyl)propiolic acid and (4-decylaminophenyl)propiolic acid.

EXAMPLE 10

Ethyl 5-(p-hexadecylaminophenyl)-2,4-pentadienoate

A sample of p-aminobenzonitrile is treated at 135° for 15 hours with equimolar quantities of 1-bromohexadecane and anhydrous potassium carbonate in hexamethylphosphoramide. Upon cooling the mixture is diluted with water and extracted with ether. Evaporation of the ether extracts and recrystallization of the residue yields p-(hexadecylamino)benzonitrile.

A solution of 11.4 g. of p-(hexadecylamino)benzonitrile in 150 ml. of toluene under nitrogen is treated with 52.5 ml. of diisobutylaluminum hydride (25% in toluene) by dropwise addition. After the addition is complete, the reaction is stirred for another 1 hr. The reaction is then quenched with 10 ml. of a 1:1 methanol:toluene solution, poured into 250 ml. of ice cold 10% aqueous sulfuric acid, then stirred for ½ hour and filtered through celite. The aqueous phase is neutralized with 5 N aqueous sodium hydroxide. The organic phase is separated, washed with water, dried and evaporated, yielding p-(hexadecylamino)benzaldehyde.

To a mixture of 0.2 mole (50% dispersion in mineral oil) of sodium hydride in 350 ml. of 1,2-dimethoxyethane cooled to 10° is added dropwise 0.2 mole of triethyl 4-phosphonocrotonate butyrate, and the mixture is stirred for 1 hr. at room temperature. A solution of 0.2 mole of p-(hexadecylamino)benzaldehyde in 150 ml. of 1,2-dimethoxyethane is then added, maintaining the temperature below 25°. The reaction is then warmed to reflux for 1 hour, allowed to cool, then poured into water (3 liters). Extraction of the mixture with ether provides ethyl 5-(p-hexadecylaminophenyl)-2,4-pentadienoate.

In an analogous manner, the following esters are prepared: ethyl 5-(p-octadecylaminophenyl)-2,4-pentadienoate, ethyl 5-(p-dodecylaminophenyl)-2,4-pentadienoate, and ethyl 5-[4-[(1-methylpentadecyl)amino]phenyl]-2,4-pentadienoate.

EXAMPLE 11

5-(p-Hexadecylaminophenyl)-2,4-pentadienoic acid

A sample of ethyl 5-(p-hexadecylaminophenyl)-2,4-pentadienoate is hydrolyzed according to Example 2 to yield 5-(p-hexadecylaminophenyl)-2,4-pentadienoic acid.

Also prepared in an analogous manner by hydrolysis of their respective esters are: 5-(p-octadecylaminophenyl)-2,4-pentadienoic acid, 5-(p-dodecylaminophenyl)2,4-pentadienoic acid, and 5-[4-[(1-methylpentadecyl)amino]phenyl]-2,4-pentadienoic acid.

EXAMPLE 12

(4-Hexadecylaminophenyl)pyruvic acid

A mixture of 0.10 mole of methyl p-aminophenylpyruvate, 0.10 mole of 1-bromohexadecane, and 0.10 mole of anhydrous potassium carbonate in 40 ml. of hexamethylphosphoramide is heated at 80° C. for 20 hrs. The mixture is then cooled, diluted with water and extracted with ether. The ethereal solution is then evaporated, yielding methyl (4-hexadecylaminophenyl)pyruvate.

A mixture of 5 g. of methyl (4-hexadecylaminophenyl)pyruvate, 5 g. of potassium hydroxide and 50 ml. of a 1:1 ethanol:water solution is heated to 50° for 3 hrs. While hot, the reaction mixture is neutralized with acetic acid and cooled. The precipitate is collected, dried and recrystallized, yielding (4-hexadecylaminophenyl)pyruvic acid.

In a like manner, (4-heptadecylaminophenyl)pyruvic acid, (4-tetradecylaminophenyl)pyruvic acid, and [4-[(13,13-dimethyltetradecyl)amino]phenyl]pyruvic acid are prepared.

EXAMPLE 13

4-(4-Hexadecylaminophenyl)-2-oxo-butyric acid

A solution of 0.1 mole of 4-hexadecylaminohydrocinnamic acid in 500 ml. of methylene chloride is stirred under reflux while a stream of hydrogen chloride gas is bubbled in. After one hour 0.1 mole of thionyl chloride is added, and stirring is continued for another hour. The solvent is evaporated in vacuo and the residue is dissolved in methylene chloride and the solution is cooled to 0°. A 50% aqueous sodium cyanide solution is added and the two-phase system is stirred for 12 hours at 0° in the presence of a catalytic quantity of tetrabutylammonium bromide. Separation of the layers and evaporation of organic phase yields crude 4-hexadecylaminohydrocinnamoyl cyanide. This material is hydrolyzed with concentrated hydrochloric acid in an ethanol-water solution to provide the title compound.

EXAMPLE 14

Ethyl p-aminophenylglyoxylate

A solution of 10 g. of ethyl p-nitrophenylglyoxylate in 10.0 ml. of ethanol is hydrogenated at room temperature and atmospheric pressure with 10% palladium-on-carbon catalyst until the starting material has disappeared by thin-layer chromatographic analysis. The system is purged with nitrogen, the reaction mixture is filtered through a celite pad and the solvent is evaporated. Recrystallization of the residue provides ethyl p-aminophenylglyoxylate.

EXAMPLE 15

(4-Hexadecylaminophenyl)glyoxylic acid

A sample of ethyl p-aminophenylglyoxylate is N-alkylated and then hydrolyzed by the method of Example 5, providing (4-hexadecylaminophenyl)glyoxylic acid.

In a similar manner, the following acids are prepared: (4-heptadecylaminophenyl)glyoxylic acid, [4-[(11-methyldodecyl)amino]phenyl]glyoxylic acid, and [4-[(14-methylpentadecyl)amino]phenyl]glyoxylic acid.

EXAMPLE 16

2-(4-Hexadecylaminophenyl)ethanol

A mixture of 1.0 g. of lithium aluminum hydride in 20 ml. of dry ethyl ether is stirred at room temperature as a solution of 5.0 g. of ethyl (4-hexadecylaminophenyl)acetate in 15 ml. of dry ethyl ether is slowly added. When the addition is complete, the reaction is stirred for an additional 2 hours and then quenched with 10% aqueous ammonium chloride. The mixture is filtered through celite, the phases are separated, and the ether is evaporated to provide 2-(4-hexadecylaminophenyl)ethanol.

In an analogous manner, the following compounds are prepared: 2-(4-nonadecylaminophenyl)ethanol, 2-(4-pentadecylaminophenyl)ethanol, 2-(4-decylaminophenyl)ethanol, 2-(4-octylaminophenyl)ethanol, 2-[4-[(1-methylpentadecyl)amino]phenyl]ethanol, 2-[4-[(2,4,6,8-tetramethylnonyl)amino]phenyl]ethanol, and 2-[4-(15-methylhexadecyl)amino]phenyl]ethanol.

EXAMPLE 17

3-(4-Hexadecylaminophenyl)propanol

By a method analogous to that described in Example 16, ethyl 4-hexadecylaminohydrocinnamate is reduced with lithium aluminum hydride to provide the title compound.

EXAMPLE 18

4-(Hexadecylamino)hydrocinnamoyl chloride hydrochloride

A solution of 37.6 g. of 4-hexadecylaminohydrocinnamic acid, prepared as described in Example 4, in 1200 ml. of methylene chloride and 300 ml. of 1,2-dimethoxyethane is stirred under reflux while hydrogen chloride gas is bubbled in for 1 hour. The mixture is then treated with 65.5 g. of thionyl chloride and stirred under reflux for another 1 hour. The dark solution is evaporated in vacuo to yield 4-(hexadecylamino)hydrocinnamoyl chloride hydrochloride.

In a like manner, the acids listed in Example 4 are converted to their respective acid chlorides as follows: 4-(nonadecylamino)hydrocinnamoyl chloride hydrochloride, 4-(pentadecylamino)hydrocinnamoyl chloride hydrochloride, 4-(decylamino)hydrocinnamoyl chloride hydrochloride, 4-(octylamino)hydrocinnamoyl chloride hydrochloride, 4-[(1-methylpentadecyl)amino]hydrocinnamoyl chloride hydrochloride, 4-[(2,4,6,8-tetramethylnonyl)amino]hydrocinnamoyl chloride hydrochloride, and 4-[(15-methylhexadecyl)amino]hydrocinnamoyl chloride hydrochloride.

EXAMPLE 19

Benzyl 4-(hexadecylamino)hydrocinnamate

A sample of 10.0 g. of 4-(hexadecylamino)hydrocinnamoyl chloride hydrochloride is treated with 9.5 g. of 4-dimethylaminopyridine and 2.5 g. of benzyl alcohol in 80 ml. of methylene chloride and the solution is heated to reflux for 4 hours. The reaction solution is then cooled, washed twice with water and dried over magnesium sulfate. The methylene chloride solution is passed through a pad of alumina. The filtrate is concentrated and the residue recrystallized from chloroform-hexane to yield benzyl 4-(hexadecylamino)hydrocinnamate.

Similarly, the appropriate acid chloride hydrochlorides provide benzyl 4-(nonadecylamino)hydrocinnamate, benzyl 4-(pentadecylamino)cinnamate, benzyl 4-(decylamino)hydrocinnamate, benzyl 4-(octylamino)hydrocinnamate, benzyl 4-[(1-methylpentadecyl)amino]hydrocinnamate, benzyl 4-[(14-methylpentadecyl)amino]phenylpropiolate, benzyl 4-[(2,4,6,8-tetramethylnonyl)amino]hydrocinnamate, and benzyl 4-(hexadecylamino)phenylacetate.

EXAMPLE 20

2-Pyridylmethyl 4-(hexadecylamino)hydrocinnamate

A solution of 10.0 g. 4-(hexadecylamino)hydrocinnamoyl chloride hydrochloride, 9.5 g. of 4-dimethylaminopyridine and 2.51 g. of 2-pyridylcarbinol is heated to reflux for 4 hours and worked up in a manner analogous to Example 19, providing 2-pyridylmethyl 4-(hexadecylamio)hydrocinnamate.

The reaction of the suitable acid chloride with 2-pyridylcarbinol similarly provides 2-pyridylmethyl 4-(pentadecylamino)cinnamate, 2-pyridylmethyl 4-(decylamino)hydrocinnamate, and 2-pyridylmethyl 4-[(1-methylpentadecyl)amino]phenylpropiolate.

Analogous reactions with acid chloride hydrochloride and 3- or 4-pyridylcarbinol provides the following: 3-pyridylmethyl 4-(hexadecylamino)hydrocinnamate, 3-pyridylmethyl 4-(pentadecylamino)cinnamate, 4-pyridylmethyl 4-(hexadecylamino)hydrocinnamate, and 4-pyridylmethyl 4-(pentadecylamino)phenylacetate.

EXAMPLE 21

2-Ethoxyethyl 4-(hexadecylamino)hydrocinnamate

Prepared as described in Example 18, 10.0 g. of 4-(hexadecylamino)hydrocinnamoyl chloride hydrochloride in 80. ml. of methylene chloride is treated with 9.5 g. of 4-dimethylaminopyridine and 2.1 g. of 2-ethoxyethanol, analogous to the method of Example 19. Workup and filtration through alumina provides 2-ethoxyethyl 4-(hexadecylamino)hydrocinnamate.

Also prepared in a similar manner from the requisite acid chloride hydrochloride are: 2-ethoxyethyl 4-(nonadecylamino)hydrocinnamate, 2-ethoxyethyl 4-(pentadecylamino)cinnamate, 2-ethoxyethyl 4-(decylamino)hydrocinnamate and 2-ethoxyethyl 4-[(1-methylpentadecyl)amino]phenylpropiolate.

EXAMPLE 22

2-Dimethylaminoethyl 4-(hexadecylamino)hydrocinnamate

As in the method of Example 21, 4-(hexadecylamino)hydrocinnamoyl chloride hydrochloride is treated with 2-dimethylaminoethanol to provide 2-dimethylaminoethyl 4-(hexadecylamino)hydrocinnamate.

In a similar fashion, the following esters are derived from acid chloride precursors: 2-dimethylaminoethyl 4-(nonadecylamino)cinnamate, 2-dimethylaminoethyl 4-(pentadecylamino)hydrocinnamate and 2-dimethylaminoethyl 4-[(1-methylpentadecyl)amino]phenylpropiolate.

EXAMPLE 23

2,3-Dihydroxypropyl 4-(hexadecylamino)hydrocinnamate

A solution of 10 g. 4-(hexadecylamino)hydrocinnamic acid, 1.0 g. of glycerol, and 10 ml. of boron trifluoride etherate in 200 ml. of toluene is stirred under reflux for 72 hours.

Dilution with water and extraction of the product with methylene chloride affords 2,3-dihydroxypropyl 4-(hexadecylamino)hydrocinnamate.

The following compounds are also prepared in a similar fashion by treatment of the necessary carboxylic acid with glycerol: 2,3-dihydroxypropyl 4-(nonadecylamino)hydrocinnamate, 2,3-dihydroxypropyl 4-(pentadecylamino)hydrocinnamate, 2,3-dihydroxypropyl (4-hexadecylaminophenyl)acetate, 2,3-dihydroxypropyl (4-pentadecylaminophenyl)acetate, 2,3-dihydroxypropyl (4-decylaminophenyl)acetate, 2,3-dihydroxypropyl 4-(4-hexadecylaminophenyl)butyrate, 2,3-dihydroxypropyl 4-(4-pentadecylaminophenyl)butyrate, 2,3-dihydroxypropyl 4-(4-octylaminophenyl)butyrate, and 2,3-dihydroxypropyl [4-[(14-methylpentadecyl)amino] phenyl]butyrate.

EXAMPLE 24

2-Phenyl-1,3-dioxan-5-yl 4-(hexadecylamino)hydrocinnamate

A solution of 450 mg. of 1,3-benzylideneglycerol and 1.22 g. of 4-dimethylaminopyridine in 10 ml. of methylene chloride is treated with 1.16 g. of 4-(hexadecylamino)hydrocinnamoyl chloride hydrochloride. After 15 minutes, the solution is washed with water, dried over anhydrous magnesium sulfate and evaporated, providing the title compound.

EXAMPLE 25

2-Hydroxy-1-(hydroxymethyl)ethyl 4-(hexadecylamino)hydrocinnamate

A mixture of 2-phenyl-1,3-dioxan-5-yl 4-(hexadecylamino)hydrocinnamate, 10% palladium-on-carbon and acetic acid is treated with hydrogen in a Parr apparatus at room temperature until hydrogen uptake ceases. The mixture is filtered and the filtrate is evaporated. Recrystallization of the residue from chloroform provides the title compound.

EXAMPLE 26

2-Hydroxypropyl 4-(hexadecylamino)cinnamate

The title ester is prepared as in Example 23 by the reaction of 4-(hexadecylamino)hydrocinnamic acid with 1,2-dihydroxypropane and boron trifluoride etherate.

Similarly prepared are 2-hydroxypropyl 4-(tetradecylamino)hydrocinnamate, 2-hydroxypropyl 4-(decylamino)hydrocinnamate, 2-hydroxypropyl 4-(octylamino)hydrocinnamate, 2-hydroxypropyl 4-(hexadecylamino)cinnamate, and 2-hydroxypropyl 4-(4-hexadecylaminophenyl)butyrate.

EXAMPLE 27

3-Hydroxypropyl 4-(hexadecylamino)hydrocinnamate

As in Example 23, the title compound is prepared by the reaction of 4-(hexadecylamino)hydrocinnamic acid with 3-hydroxypropanol and boron trifluoride etherate.

Similarly, 3-hydroxypropyl 4-(tetradecylamino)hydrocinnamate, 3-hydroxypropyl (4-hexadecylaminopheny)acetate, 3-hydroxypropyl 4-(4-hexadecylaminophenyl)butyrate and 3-hydroxypropyl (4-tetradecylaminophenyl)acetate are prepared.

EXAMPLE 28

Phenyl 4-(hexadecylamino)hydrocinnamate

A solution of 0.05 mole of 4-(hexadecylamino)hydrocinnamic acid and 0.05 mole of 1,1'-carbonyldiimidazole in 50 ml. of tetrahydrofuran is treated with 0.052 mole of phenol and a trace of sodium hydride. The reaction is heated to reflux for 3 hours, then cooled, filtered and evaporated in vacuo providing phenyl 4-(hexadecylamino)hydrocinnamate.

Similarly prepared from the carboxylic acid precursors are: phenyl (4-nonadecylaminophenyl)acetate, phenyl (4-heptadecylaminophenyl)acetate, phenyl (4-decylaminophenyl)acetate, phenyl [4-[(1-methylpentadecyl)amino]phenyl]acetate, phenyl 4-[(14-methylpentadecyl)amino]phenylpropiolate, phenyl 4-(nonadecylamino)hydrocinnamate, phenyl 4-(tetradecylamino)cinnamate, phenyl 4-(decylamino)hydrocinnamate, phenyl 4-(4-hexadecylaminophenyl)butyrate, phenyl 4-(4-tridecylaminophenyl)butyrate, 4-carboethoxyphenyl 4-(hexadecylamino)hydrocinnamate, and 4-carboxyphenyl 4-(hexadecylamino)cinnamate.

EXAMPLE 29

3-Pyridyl 4-(hexadecylamino)hydrocinnamate

In a manner analogous to that described in Example 28, 4-(hexadecylamino)hydrocinnamic acid is esterified with 3-hydroxypyridine to provide 3-pyridyl 4-(hexadecylamino)hydrocinnamate. Similarly prepared are 3-pyridyl (4-heptadecylaminophenyl)acetate, 3-pyridyl 4-(decylamino)phenylpropiolate, 3-pyridyl 4-(nonadecylamino)hydrocinnamate, 3-pyridyl 4-(tetradecylamino)hydrocinnamate, 3-pyridyl (4-hexadecylaminophenyl)butyrate, 3-pyridyl (4-tridecylaminophenyl) 5-carboethoxy-3-pyridyl 4-(hexadecylamino)hydrocinnamate, and 5-carboxy-3-pyridyl 4-(hexadecylamino)cinnamate.

EXAMPLE 30

Carboxymethyl 4-(Hexadecylamino)hydrocinnamate

A solution of the sodium salt of 4-(hexadecylamino)hydrocinnamic acid (0.01 mole), methyl chloroacetate (0.1 mole) and 50 ml. of hexamethylphosphoramide is heated to 125° for 5 hours. The solution is then cooled and diluted with water and ether. The ether phase is separated, washed with two portions of water, dried and evaporated. Recrystallization of the residue provides the carbomethoxymethyl ester. This ester is selectively hydrolyzed with 1.5 equivalents of warm 0.1 N 90% ethanolic sodium hydroxide for 2 hours. Cooling and acidification with 0.1 N hydrochloric acid yields the white crystalline title compound.

Similarly prepared is carboxymethyl 4-(hexadecylamino)phenylacetate and carboxymethyl 4-(hexadecylamino)cinnamate.

EXAMPLE 31

2-(4-Hexadecylaminophenyl)aetamide

A solution of (4-hexadecylaminophenyl)acetic acid is converted to the corresponding acid chloride hydrochloride as described in Example 18.

A sample of (4-hexadecylaminophenyl)acetyl chloride hydrochloride is slurried in methylene chloride at 0° as anhydrous ammonia gas is bubbled in for one half hour. At the end of this time, the reaction mixture is washed with water and then aqueous sodium bicarbonate. The organic phase is then dried, filtered and evaporated, providing 2-(4-hexadecylaminophenyl)acetamide.

EXAMPLE 32

4-(Hexadecylamino)hydrocinnamamide

As in the method described in Example 31, 4-(hexadecylamino)hydrocinnamic acid chloride hydrochloride is treated with anhydrous ammonia to yield 4-(hexadecylamino)hydrocinnamamide.

EXAMPLE 33

(4-Hexadecylaminophenyl)acetonitrile

A solution of 2-(4-hexadecylaminophenyl)acetamide in benzene is cooled to 10° and a stream of dry hydrogen chloride gas is bubbled in. After one-half hour an excess of thionyl chloride is added and the reaction is heated to reflux for five hours. The reaction is then cooled in ice and poured into a slurry of ice and water. Cold 50% aqueous potassium hydroxide is slowly added until the mixture is basic to litmus. The layers are then separated and the aqueous portion is extracted with more benzene. The combined benzene extracts are washed with aqueous sodium carbonate and then with water. Evaporation of the solvent and recrystallization of the residue from hexane gives (4-hexadecylaminophenyl)acetonitrile.

In an analogous fashion, 4-(hexadecylamino)hydrocinnamamide is converted to 4-(hexadecylamino)hydrocinnamonitrile.

EXAMPLE 34

4-(4-Hexadecylaminophenyl)butyramide

A sample of 4-(4-hexadecylaminophenyl)butyric acid is converted via its acid chloride hydrochloride to the title compound by the procedure described in Example 31.

EXAMPLE 35

4-(Hexadecylamino)cinnamaldehyde

A solution of 10.0 g. of 4-hexadecylaminohydrocinnamonitrile in 100 ml. of dry ether is added rapidly to a mixture of 10.2 g. of anhydrous stannous chloride and 80 ml. of ether which has been saturated with dry hydrogen chloride for 2 hours. Dry hydrogen chloride is again bubbled through the reaction mixture which is stirred for 1 hour and allowed to stand for 20 hours. The ethereal solution is decanted from the semi-solid product which is washed again with ether and then treated with water and heated to reflux for 3 hours. Cooling and extraction of the reaction mixture with ether provides 4-(hexadecylamino)cinnamaldehyde.

EXAMPLE 36

4-(Hexadecylamino)cinnamonitrile

A mixture of p-aminobenzoylacetonitrile, 1-bromohexadecane, potassium carbonate and hexamethylphosphoramide is heated to 80° C. for 20 hours and worked up as in Example 1, providing 4-hexadecylaminobenzoylacetonitrile. This material is dissolved in isopropanol and treated with an excess of sodium borohydride. After stirring at room temperature for 3 hours, the solution is concentrated, diluted with water and extracted with chloroform. The chloroform extract yields the crude carbinol which is heated to reflux for 1 hour with ethanol containing an equal volume of 2 N aqueous hydrochloric acid. The solution is then cooled, diluted with water and extracted with chloroform. The organic extract is washed successively with water and aqueous sodium bicarbonate, then dried and evaporated to afford 4-(hexadecylamino)cinnamonitrile.

EXAMPLE 37

4-(Hexadecylamino)phenylpropiolamide

A solution of 4-hexadecylaminophenylpropiolic acid is converted to 4-hexadecylaminophenylpropiolic acid chloride hydrochloride as described in Example 18. After evaporation of the solvent, the unpurified acid chloride is slurried in methylene chloride and treated with anhydrous ammonia as in Example 31. Workup as described therein provides the title compound. Likewise, 4-(hexadecylamino)cinnamamide is prepared from 4-(hexadecylamino)cinnamic acid.

EXAMPLE 38

4-(Hexadecylamino)phenylpropiolonitrile

As described in Example 33, a sample of 4-hexadecylaminophenylpropiolamide is treated successively with hydrogen chloride gas and refluxing thionyl chloride to afford 4-(hexadecylamino)phenylpropiolnitrile. Similarly prepared is 4-(4-hexadecylaminophenyl)butyronitrile.

EXAMPLE 39

4-(Hexadecylamino)cinnamaldehyde

As in Example 35, 4-hexadecylaminocinnamaldehyde is prepared by stannous chloride reduction of 4-hexadecylaminocinnamonitrile. Similarly prepared from their respective nitriles are 4-(hexadecylamino)phenylacetaldehyde and 4-(4-hexadecylaminophenyl)butyraldehyde.

EXAMPLE 40

3-Carboxy-2-hydroxypropyl 4-(hexadecylamino)cinnamate

By the method described in Example 21, glyceric acid is employed to prepare 3-carboxy-2-hydroxypropyl 4-(hexadecylamino)cinnamate.

EXAMPLE 41

Preparation of 2,3-dihydroxypropyl-4-(hexadecylamino)phenylacetamide

A slurry of 8.0 g. of 4-(hexadecylamino)phenylacetic acid hydrochloride in 175 ml. of methylene chloride and 50 ml. of glyme containing 10 ml. of thionyl chloride is heated at reflux for 2 hours. The clear solution is concentrated in vacuo giving 9.5 g. of an amber oil. This oil is dilutd with 50 ml. of pyridine containing 0.1 g. of 4-dimethylaminopyridine and 9.1 g. of 3-amino-1,2-propanediol. The reaction is stirred for two days at room temperature. The solution is partitioned between ether and water. The water phase is extracted twice more with 100 ml. of chloroform and ether. The combined organic layer is extracted with water, dried over magnesium sulfate and evaporated to a tacky solid. The solid is recrystallized from acetone-water and then from benzene.

Similarly prepared are the 4-(p-hexadecylaminophenyl)butyryl and 4-(hexadecylamino)cinnamoyl 2,3-dihydroxypropylamides.

EXAMPLE 42

Preparation of 1-[4-(hexadecylamino)phenylacetyl] piperidide

To a chilled solution of 35 ml. of piperidine, 2.5 ml. of triethylamine and 0.6 g. of dimethylaminopyridine in 100 ml. of diethyl ether is added (178 hour) a solution of 8.3 g. of 4-(hexadecylamino)phenylacetyl chloride in 50 ml. of methylene chloride. The solution is warmed to room temperature and maintained there for two hours. The solution is heated to reflux for an additional 2 hours at which time the reaction is complete. The solution is cooled, extracted twice with 100 ml. portions of water and dried over magnesium sulfate. The solvent is removed in vacuo and the solid recrystallized from 50 ml. of diethyl ether.

Prepared similarly are the 4-(pentadecylamino)-phenylpropionyl, 4-(tetradecylamino)cinnamoyl, and 4-(hexadecylamino)phenylpropiolyl piperidides.

EXAMPLE 43

Preparation of N-[4-(pentadecylamino)cinnamoyl] 2,3-dihydroxypropylamine

To a mixture containing 4.3 g. of 1-[N-(t-butyloxycarbonyl)-4-(pentadecylamino)cinnamoyl] imidazole, 50 ml. of chloroform, and 50 ml. of 5 N sodium hydroxide is added 1.1 g. of 3-amino-1,2-propanediol. The solution is vigorously stirred for 24 hours, the layers are separated, and the chloroform solution is washed once with 50 ml. of 1 N sodium hydroxide. The solvent is evaporated and the residue is heated for 30 minutes at 40° C. in 50 ml. of anhydrous trifluoroacetic acid. The solvent is again evaporated and the oil is crystallized from acetone to yield light yellow crystals.

By the same procedure are prepared the 4-(hexadecylamino)phenylpropiolyl and 4-(tetradecylamino)-hydrocinnamoyl 2,3-dihydroxypropylamines.

EXAMPLE 44

Preparation of 1-[4-(N-t-butyloxycarbonyl-N-pentadecylamino)cinnamoyl] imidazole To a solution of 10 g. 4-(pentadecylamino)cinnamic acid in 100 ml. dioxane is treated with 4.0 g. t-butylazidoformate and 10 ml. pyridine. After stirring at room temperature for 18 hours, the protected amidoacid is precipitated from solution by addition of 150 ml. water. The product is collected and thoroughly dried. The crude product is dissolved in 200 ml. of a mixture consisting of methylene chloride/dimethoxyethane/-pyridine (1:4:1), and to this is added 5.4 g. 1,1'-carbonyl-diimidazole. The solution is stirred overnight at room temperature and the solvents are evaporated to yield the title compound as a thick, orange oil.

EXAMPLE 45

Preparation of N-trifluoroacetyl-4-(hexadecylamino)phenylpropiolyl chloride

To a stirred, ice-cold suspension of 9 g. 4-(hexadecylamino)phenylpropiolic acid in 100 ml. dimethoxyethane and 16 ml. pyridine is treated with 18 ml. trifluoroacetic anhydride. The solution is stirred at 0° C. for 30 minutes at room temperature. The solution is diluted with 300 ml. ether and 100 g. ice. After stirring vigorously for 15 minutes, the phases are separated, the ether solution is washed with brine, dried and evaporated to a white, amorphous solid.

To 9.2 g. of the above product in 30 ml. methylene chloride and 0.5 ml. dimethylformamide is added 5.7 ml. thionyl chloride. After 20 hours at reflux the solvents are evaporated to yield a light yellow, mobile oil.

EXAMPLE 46

Preparation of diethyl O-[4-(hexadecylamino)phenylpropiolyl]tartrate

N-trifluoroacetyl-4-(hexadecylamino)phenylpropiolyl chloride and 1.2 g. triethylamine in 100 ml. warm ether is treated with 2.5 g. diethyl tartrate and refluxed for 24 hours. The hot solution is filtered, the residue is washed with hot ether, and the solution is evaporated. After treatment with aqueous methanolic potassium carbonate, the product is precipitated by acidification, filtered, and dried. Crystallization from acetone yields the diethyl tartrate derivative as a white, crystalline solid.

EXAMPLE 47

N-Carbobenzyloxy-4-(hexadecylamino)cinnamoyl chloride

To 15 g. 4-(hexadecylamino)cinnamic acid in 200 ml. warm chloroform is added 15 g. sodium carbonate in 150 ml. water. To the vigorously stirred solution is added 10 g. carbobenzyloxy chloride. After 2 hours stirring at 40° C., the layers are separated, washed three times with 1 N hydrochloric acid, dried, and evaporated to an oil. The oil is dissolved in 300 ml. toluene, treated with 15 ml. thionyl chloride and the solution is refluxed for 5 hours. The solvents are evaporated and the residue is dissolved three times in toluene, evaporating each time to yield a viscous, orange oil.

EXAMPLE 48

Preparation of O-[4-(hexadecylamino)hydrocinnamoyl]malic acid

To a warm solution of N-carbobenzyloxy-4-(hexadecylamino)cinnamoyl chloride and 1.3 g. triethylamine in 100 ml. ether is treated with 2 g. malic acid. An immediate precipitate forms, but the mixture is refluxed for one hour and filtered while hot. The solid is washed several times with hot ether, then the ether is evaporated to yield a white solid. The product is dissolved in tetrahydrofuran (100 ml.) and hydrogenated over 600 mg. 10% Pd(C) at 50 psi until hydrogen uptake stops. The catalyst is filtered, the solution is evaporated and the residue is crystallized from acetic acid to yield the reduced and deblocked title compound as a tan, crystalline mass.

EXAMPLE 49

Preparation of diethyl O-[4-(hexadecylamino)cinnamoyl]malate

In a manner similar to Example 48, a solution of 6.0 g. N-carbobenzyloxy-4-(hexadecylamino)cinnamoyl chloride and 1.2 g. triethylamine in 100 ml. warm ether is treated with 2.3 g. diethyl malate. After one hour at reflux, the precipitate is filtered and washed with warm ether. After evaporation to dryness, the intermediate is dissolved in 50 ml. 30% hydrobromic/acetic acid and warmed at 50° C. for 2 hours. The solvents are evaporated and the product is partitioned between methylene chloride and water. The layers are separated and the methylene chloride is evaporated. The residue is crystallized from acetone to yield colorless crystals.

EXAMPLE 50

Preparation of N-[4-(hexadecylamino)cinnamoyl]-2-aminoethanesulfonic acid

To a stirred solution of 2.50 g. of taurine and 5.6 ml. of triethylamine in 22.5 ml. of water is added 4.4 g. of p-(2,2,2-trifluoro-N-hexadecylacetamido)cinnamoyl chloride as a solution in 45 ml. of ethanol. After 24 hours, the mixture is treated with 20 ml. of 2.0 M sodium hydroxide and 25 ml. of water. After stirring for 10 min., the mixture is acidified with dilute hydrochloric acid, and the crude product is collected by filtration. Recrystallization affords the title compounds as white solid.

Similarly prepared are the following taurine amides: 4-(hexadecylamino)phenylpropiolyl, 4-(hexadecylamino)hydrocinnamoyl, and 4-(hexadecylamino)phenylacetyl taurine amides.

EXAMPLE 51

Preparation of 3-[4-(hexadecylamino)cinnamoyl]-4-carboethoxy thiazolidine

One-tenth mole of 4-(hexadecylamino)cinnamoyl chloride hydrochloride in methylene chloride is added to a solution of 0.1 mole of ethyl thiazolidine-4-carboxylate in chloroform containing two equivalents of triethylamine. After 5 hours at 20° C. the solution is filtered and evaporated to a white solid which is recrystallized from acetonitrile.

EXAMPLE 52

Preparation of 3-[4-(hexadecylamino)cinnamoyl]-4-carboxythiazolidine

By means of the alkaline hydrolysis method of Example 54, the ethyl ester of Example 51 is converted to the subject carboxylic acid. This acid is also prepared using the procedure of Example 51 except that the acylation of the thiazolidine-4-carboxylic acid is carried out in aqueous acetone sodium bicarbonate solution.

EXAMPLE 53

Preparation of ethyl 4-(hexadecylamino)phenylacetyl glycinate

To a solution of 18.0 g. of 4-(hexadecylamino)phenylacetic acid in a mixture of dioxane and methylene chloride (40 ml./160 ml.) is added gaseous HCl for 10 minutes. The slurry is cooled and 18 ml. of thionylchloride added. The slurry is brought to reflux for 2 hours and then concentrated under vacuum (thrice, diluting with dioxane each time). The final amber solution is diluted with 100 ml. of dioxane and this solution added to freshly prepared ethyl glycinate in 300 ml. of methylene chloride containing 1 g. of dimethylaminopyridine and 10 ml. of triethylamine. After 16 hours at room temperature, the reaction mixture is refluxed for 2 hours, cooled and filtered. The mother liquor is extracted with water and 10% hydrochloric acid. The solution is dried and concentrated in vacuo to an amber liquid, 18.97 g. which is chromatographed on 450 g. of silica by eluting with ether to give 4.2 g. of solid. This material is recrystallized from acetonitrile.

EXAMPLE 54

Preparation of N-[4-(hexadecylamino)phenylacetyl]glycine

A mixture of 26.4 g. of ethyl N-[4-(hexadecylamino)phenylacetyl]glycinate, 110 ml. of 1 N sodium hydroxide solution; and 100 ml. of ethanol is stirred at ambient temperature for 2 hours and then partially evaporated. The aqueous solution is washed with diethyl ether, acidified with 6 N hydrochloric acid, and filtered. The white solid is dried in vacuo and recrystallized from acetone.

The 4-(4-hexadecylaminophenyl)butyryl analog is prepared by ethyl glycinate acylation and hydrolysis in the same fashion.

EXAMPLE 55

Preparation of 3-bromopropyl-4-(hexadecylamino)phenylacetamide

To a slurry of 21.80 g. of 3-bromopropylamine hydrobromide in 200 ml. of glyme at 3° C. is added a solution of 23.96 g. of 4-(hexadecylamino)phenylacetyl chloride hydrochloride in 65 ml. of glyme, concurrently with 26 ml. of triethylamine diluted to 39 ml. with glyme. The solution is warmed to reflux and 0.2 g. of 4-dimethylaminopyridine is added. The solution is heated for four hours and cooled overnight. The solid is removed and the mother liquor diluted with 200 ml. of water giving 12.94 g. The solid is recrystallized from cyclohexane and is then chromatographed on silica gel by elution with chloroform. The largest component is recrystallized from acetronitrile.

EXAMPLE 56

Preparation of 2-[4-(hexadecylamino)benzyl]-5,6-dihydro[4H]-1,3-oxazine

To 0.4 g. of sodium hydride in 100 ml. of glyme is added 2.14 g. of N-(3-bromopropyl)-4-(n-hexadecylamino)phenylacetamide and 12 ml. of triethylamine. The turbid solution is heated to reflux for 20 hours. The solution is diluted with 100 ml. of water and cooled overnight. The solid is collected, washed with water and oven dried giving 2 g. of solid which gives a negative AgNO$_3$ test and halogen flame test. This solid is recrystallized from cyclohexane giving 1.68 g. of solid which then is recrystallized from acetonitrile giving white crystals.

EXAMPLE 57

Preparation of
2-[4-(hexadecylamino)phenylethylene]oxazoline

To a slurry of 15 g. of 2-bromoethylamine hydrobromide in 150 ml. of glyme is added simultaneously solutions of 31 g. of 4-(hexadecylamino)cinnamoyl chloride hydrochloride in 60 ml. of glyme and 50 cc. of triethylamine (dropwise). After addition of 0.5 g. of 4-dimethylaminopyridine the mixture is stirred at room temperature overnight. The solution is refluxed for one hour and filtered. The solid is oven dried and partitioned between methylene chloride and water. The layers are separated and the organic phase dried. The organic layer is concentrated to about 100 ml. and diluted with an equal volume of hexane. The product (4.15 g.) is chromatographed on a silica III column and recrystallized from cyclohexane and then from acetronitrile.

EXAMPLE 58

Preparation of
N-[(4-hexadecylamino)hydrocinnamoyl]benzamide

One gram of a 50% oil dispersion of sodium hydride is washed with hexane by decantation and suspended in 5 ml of tetrahydrofuran. To this stirred mixture is added a solution of 2.42 g of benzamide in 5 ml. of tetrahydrofuran. An initial hydrogen evolution is observed. While stirring (30 min.), the sodium hydride gradually disappears and forms a white-milky turbid mixture. Then a solution of 4.8 g. of N-trifluoroacetyl-4-(hexadecylamino)hydrocinnamoyl chloride in 20 ml. of tetrahydrofuran is added dropwise during 5 minutes. The mixture is stirred at room temperature under nitrogen for one hour. The whole reaction mixture is poured into water and, after about one hour, extracted with ether twice. The ether extract is washed with water, brine, and dried over anhydrous sodium sulfate. After evaporation of solvent, it gives a pale yellow solid. The solid is dissolved in hot ether/acetonitrile (50/50) and, after standing overnight at room temperature, the collected solids are recrystallized from hot acetonitrile to give pale yellow crystals.

EXAMPLE 59

Preparation of
p-hexadecylamino-N-(phenylsulfonyl)hydrocinnamoylamide

A solution of 31.4 g. of benzenesulfonamide in 250 ml. of dry dimethylacetamide is added dropwise, with stirring and cooling, to a suspension of 5.5 g. of sodium hydride in 100 ml. of dry dimethylacetamide over 30 minutes at room temperature. Stirring is continued for a further 30 minutes. In the meantime, a mixture of 38.0 g. of p-hexadecylaminohydrocinnanic acid in 1200 ml. of methylene chloride, 300 ml. of dimethoxyethane, and 40 ml. of thionyl chloride is refluxed for 1 hour and 15 minutes. The solution is evaporated to an oil which is co-evaporated twice with added dioxane to remove excess thionyl chloride. To the resulting oily residue of p-(hexadecylamino)hydrocinnamoyl chloride hydrochloride is added, in one portion, the previously prepared mixture of sodium benzenesulfonamide in dimethylacetamide. The mixture is stirred for 30 minutes, without cooling, and is then filtered through a bed of diatomaceous earth. The filtrate is poured into 2 l. of water, and 250 ml. of saturated sodium chloride solution added to coagulate the precipitate. The mixture is filtered and the product is washed with water and partially air dried. The product is dissolved in methylene chloride, the mixture is filtered through diatomaceous earth, and brine is added to break the emulsion. The layers are separated, the organic phase is dried over anhydrous sodium sulfate and filtered through a bed of 300 g. of hydrous magnesium silicate. The product is eluted with an additional 3 l. of methylene chloride. The first approx. 1 l. of filtrate is set aside and the remainder is evaporated to dryness. The residue is crystallized three times from toluene and the product is dried at 65° C. to provide the title compound as colorless crystals.

EXAMPLE 60

Preparation of
p-Hexadecylamino-N-(methylsulfonyl)cinnamoylamide

A solution of 19.0 g. of methanesulfonamide in 150 ml. of dry dimethylacetamide is added dropwise over 15 minutes to a stirred and cooled (water bath) suspension of 5.5 g. of sodium hydride in 100 ml. of dry dimethylacetamide. The mixture is then stirred and heated at 60°–80° C. for 2 hours. In the meantime, a mixture of 38.0 g. of p-(hexadecylamino)cinnamic acid in 1200 ml. of methylene chloride, 300 ml. of dimethoxyethane, and 40 ml. of thionyl chloride is converted to p-(hexadecylamino)cinnamoyl chloride hydrochloride and reacted as in Example 59. After isolating the product similarly, it is recrystallized twice from dioxane and dried in the Abderhalden at 65° C. to give 12.0 g. of the title compound as tan crystals.

EXAMPLE 61

Preparation of
p-Hexadecylamino-N-(p-tolylsulfonyl)phenylpropiolyl amide

A solution of 34.25 g. of p-toluenesulfonamide in 250 ml. of dry dimethylacetamide is added dropwise over 30 minutes to a stirred and cooled (water bath) suspension of 5.5 g. of sodium hydride in 100 ml. of dry dimethylacetamide. Stirring is continued at room temperature for 3 hours until foaming subsides. In the meantime, a mixture of 37.8 g. of p-(hexadecylamino)phenylpropiolic acid in 1200 ml. of methylene chloride, 300 ml. of dimethoxyethane, and 40 ml. of thionyl chloride is converted to p-(hexadecylamino)phenylpropiolyl chloride, reacted and isolated as in Example 59. The filtrate is concentrated on the steam bath to approximately 300 ml. and is filtered through 300 g. of hydrous magnesium silicate using 3 l. of methylene chloride as eluant. The first 600 ml. of filtrate is discarded and the remainder is evaporated to a tan, pasty solid. The solid is crystallized from 75 ml. of 2:1 toluene:hexane solution to give a colorless solid containing a less polar by-product. The mixture is crystallized from absolute ethanol and crystallized twice from 2:1 toluene:hexane to give the title compound as colorless crystals.

EXAMPLE 62

2,3-Dihydroxypropyl 4-(hexadecylamino)cinnanate

A solution of 7.34 g. of 4-(hexadecylamino)cinnanic acid, 4.80 g. of 25% aqueous sodiumhydroxide, and 12.6 g. of 3-iodo-1,2-propanediol in 50 ml of hexamethylphosphoramide is stirred for 24 hours at ambient temperature, diluted with 100 ml of ether and stirred for 5 days at ambient temperature. The mixture is treated with water and extracted with ether. The dried extracts are evaporated to yield 2,3-dihydroxypropyl 4-(hexadecylamino)cinnate.

EXAMPLE 63

Preparation of 15-methylhexadecyl bromide

A solution of 3-methylbutylmagnesium bromide is prepared by treating 15.1 g. of 3-methylbutyl bromide with 2.7 g. of magnesium turnings in 50 ml. dry tetrahydrofuran. The resultant Grignard reagent is dropwise added to a cold ($-10°$ C.) solution of 36.1 g. of 1,12-dibromododecane and 0.2 g. of lithium tetrachlorocuprate in 75 ml. dry tetrahydrofuran. The solution is stirred for 1 hour, evaporated, and fractionally distilled in vacuo to yield 15-methylhexadecyl bromide as a colorless liquid.

EXAMPLE 64

Preparation of 14-methylpentadecyl bromide

By a procedure analagous to that described in Example 1, 3-methylbutylmagnesium bromide in tetrahydrofuran is reacted with 34.5 g. of 1,11-dibromoundecane and 0.2 g. of $Li_2CuCl_4$ in 75 ml. tetrahydrofuran. After one hour stirring at $-10°$ C., the solution is evaporated and the resultant oil is distilled in vacuo to yield the colorless 14-methylpentadecyl bromide.

EXAMPLE 65

Preparation of 13,13-dimethyltetradecyl bromide

A solution of t-butylmagnesium bromide is prepared by reacting 13.7 g. of t-butyl bromide with 2.67 g. of magnesium turnings in 50 ml. dry tetrahydrofuran. The solution of Grignard reagent is dropwise added to a stirred, cold ($-10°$ C.) solution of 36.1 g. of 1,12-dibromododecane and 0.2 g. of dilithiumetetrachlorocuprate in 75 ml. dry tetrahydrofuran at a rate such that the reaction temperature does not exceed $-50°$ C. After one additional hour of stirring at $-10°$ C., the solvent is evaporated and the resultant liquid is fractionated in vacuo to yield 13,13-dimethyltetradecyl bromide as a colorless liquid.

EXAMPLE 66

Preparation of Ethyl 4-(p-hexadecylamino)phenylisobutyrate

The reagents 12.2 g. of 1-bromohexadecane, 8.28 g. of ethyl 2-(4a-aminophenyl)isobutyrate, 5.25 g. of potassium carbonate, and 80 ml. of hexamethylphosphoramide solvent are heated under argon at 100° for 20 hours, cooled to room temperature, diluted with 10 ml. of water and chilled in a refrigerator overnight. The oil layer is separated and dissolved in 100 ml. of methylene chloride which is extracted with water. The organic layer is separated, dried, and passed through silica gel. Concentration in vacuo affords 16.91 g. brown liquid which is dissolved in 50 ml. of hexane and this solution is extracted with water. The hexane solution is dried and concentrated to give the liquid product.

EXAMPLE 67

Preparation of 4-(hexadecylamino)phenylbutyric acid

The reagents 8.2 g. of ethyl 4-(hexadecylamino)-phenylbutyrate and 3.36 g. of potassium hydroxide in 100 ml. 75% ethanol are heated to reflux for 6 hours. To the hot solution is added 5.4 ml. of concentrated hydrochloric acid, followed by 50 ml. of water. After chilling in refrigerator overnight, a white solid forms which is recrystallized from 50 ml. of 90% EtOH to afford the off-white crystalline product.

I claim:

1. A compound represented by the following structured formula:

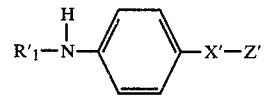

wherein X' is selected from the group consisting of an unbranched or branched $C_1-C_3$ alkylene, $C_2-C_4$ alkenylene, or ethynylene; Z' is selected from the group consisting of carboxyl, formyl, carbamoyl and $COOR_3$ wherein $R_3$ is selected from the group consisting $C_1-C_4$ branched and unbranched alkyl, $C_1-C_3$ alkoxyloweralkyl, di($C_1-C_3$ dialkyl)aminoloweralkyl, $C_1-C_3$ mono- or dihydroxyalkyl, phenyl, halophenyl, 3-pyridyl, phenylmethyl, pyridylmethyl, $C_3-C_5$ carboalkoxyalkyl, and $C_2-C_5$ carboxyalkyl and $R_1$ is a branched or unbranched alkyl group $C_nH_{2n+1}$ wherein n is an integer 13 to 17.

2. A compound according to claim 1, 4-(hexadecylamino)phenylacetic acid.

3. A compound according to claim 1, 4-(tetradecylamino)phenylacetic acid.

4. A compound, 4-(octylamino)phenylacetic acid.

5. A compound according to claim 3, 4-(hexadecylamino)hydrocinnamic acid.

6. A compound, ethyl 4-(N-hexadecylacetamido)hydrocinnamate.

7. A compound, 4-(hexadecylmethylamino)hydrocinnamic acid.

* * * * *